(12) United States Patent
Kankan et al.

(10) Patent No.: US 8,691,999 B2
(45) Date of Patent: Apr. 8, 2014

(54) PROCESS FOR THE PREPARATION OF TELMISARTAN

(75) Inventors: Rajendra Narayanrao Kankan, Mumbai (IN); Dharmaraj Ramachandra Rao, Mumbai (IN); Srinivas Laxminarayan Pathi, Bangalore (IN); Ravikumar Puppala, Bangalore (IN)

(73) Assignee: Cipla Limited, Mumbai (IN)

( * ) Notice: Subject to any disclaimer, the term of this patent is extended or adjusted under 35 U.S.C. 154(b) by 1201 days.

(21) Appl. No.: 11/568,898

(22) PCT Filed: May 10, 2005

(86) PCT No.: PCT/GB2005/001799
§ 371 (c)(1),
(2), (4) Date: Jan. 11, 2007

(87) PCT Pub. No.: WO2005/108375
PCT Pub. Date: Nov. 17, 2005

(65) Prior Publication Data
US 2008/0015359 A1    Jan. 17, 2008

(30) Foreign Application Priority Data
May 11, 2004 (GB) .................................. 0410471.7

(51) Int. Cl.
*C07D 235/20* (2006.01)
*C07D 235/06* (2006.01)
*C07D 403/02* (2006.01)

(52) U.S. Cl.
USPC ....................................................... 548/305.4

(58) Field of Classification Search
None
See application file for complete search history.

(56) References Cited

U.S. PATENT DOCUMENTS

| 5,591,762 A | 1/1997 | Hauel et al. |
| 6,358,986 B1 | 3/2002 | Schneider |
| 6,410,742 B1 | 6/2002 | Schneider |

FOREIGN PATENT DOCUMENTS

| CN | 1344712 | * | 4/2002 |
| CN | 1412183 | * | 4/2003 |
| CN | 1412183 | A | 4/2003 |
| IE | 920373 | | 8/1992 |
| WO | WO 00/27397 | | 5/2000 |
| WO | WO 00/62836 | | 10/2000 |
| WO | WO 2004/087676 | | 10/2004 |

OTHER PUBLICATIONS

Foreign communication from a related counterpart application—International Search Report, PCT/GB2005/001799, Aug. 10, 2005, 5 pages.
Foreign communication from a related counterpart application—International Preliminary Report on Patentability, PCT/GB2005/001799, Aug. 4, 2006, 8 pages.
English abstract and translation of CN 1344712 A.

* cited by examiner

*Primary Examiner* — Sun Jae Yoo
(74) *Attorney, Agent, or Firm* — Conley Rose, P.C.; Rodney B. Carroll

(57) ABSTRACT

An improved process for the preparation of telmisartan, or a pharmaceutically acceptable salt thereof, comprises subjecting 1H-Benzimidazole-2-n-propyl-4-methyl-6-(1'-methyl benzimidazole-2'yl)] of formula (II), and methyl-4-(bromomethyl)biphenyl-2-carboxylate of formula (III) to condensation and hydrolysis in a single step:

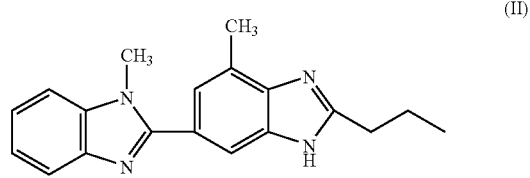

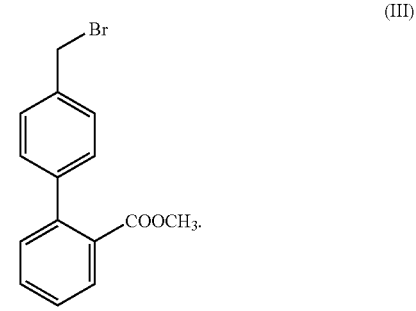

21 Claims, No Drawings

PROCESS FOR THE PREPARATION OF TELMISARTAN

CROSS-REFERENCE TO RELATED APPLICATIONS

This application is a filing under 35 U.S.C. 371 of International Application No. PCT/GB2005/001799 filed May 10, 2005, entitled "Process for the Preparation of Telmisartan," claiming priority of Great Britain Patent Application No. GB 0410471.7 filed May 11, 2004, which applications are incorporated by reference herein in their entirety.

FIELD OF THE INVENTION

The present invention relates to a process for the preparation of telmisartan[4'-[2-n-propyl-4-methyl-6-(1-methyl-benzimidazol-2-yl)benzimidazol-1-yl methyl]biphenyl-2-carboxylic acid] in a "one pot" synthesis, which is thus simple and cost effective, and produces telmisartan with high product yield and quality.

BACKGROUND OF THE INVENTION

Telmisartan is known from EP 0502314B and has the following chemical structure of formula (I):

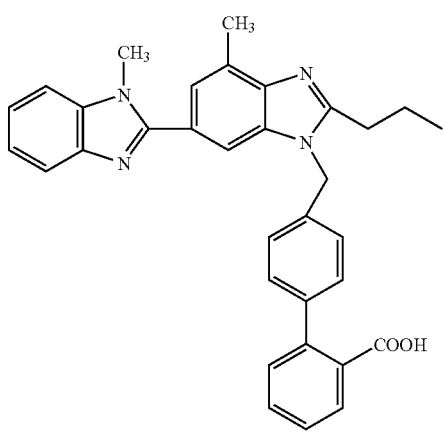

Telmisartan is an angiotensin II receptor antagonist, which by virtue of its pharmacological properties is particularly useful in the treatment of hypertension and cardiac insufficiency.

Chinese Patent CN 1344172 discloses the preparation of telmisartan in two steps: namely condensation and hydrolysis.

U.S. Pat. No. 5,591,762 discloses the preparation of telmisartan from its tertiary butyl ester. Hydrolysis is carried out using trifluoro acetic acid in dimethyl formamide at room temperature and maintained for about 12 hours. The crude product obtained is purified over a silica gel column and finally crystallized from acetone.

US 2002/0094997 is a divisional application of U.S. Pat. No. 6,358,986. US 2002/0094997 discloses polymorphs of telmisartan, particularly polymorphic form B, polymorphous mixtures and their preparation. Accordingly, telmisartan Form A is dissolved in a mixture of solvents consisting of water, formic acid and an organic solvent that is miscible therewith; the solution is heated followed by distillation and telmisartan containing Form A and Form B is precipitated from the mixture by addition of a base. The disclosure further refers to advantages of the polymorphic Form B mixture, for example it is easily filterable and has a low tendency to electrostatic charging. The disclosure still further refers to the fact that Form A, which is obtained according to the basic patent, is difficult to filter, is characterized by a very long drying time and exhibits a strong tendency to electrostatic charging. The two telmisartan polymorphs of Form A and B as characterised by US 2002/0094997 differ considerably in their melting point: Form B melts at 183° C. (determined by DSC), Form A at 269° C. (determined by DSC). The polymorphs A and B also differ in their IR spectrum. Pure polymorph A has a characteristic band at 815 cm$^{-1}$ in the IR spectrum. In polymorph B, this oscillation is shifted to 830 cm$^{-1}$.

In all the prior art processes, telmisartan is prepared in two or three steps, which is time consuming, product is lost during intermediate isolation, and as such there is a resulting low yield of the final product. It is also suggested in the prior art that the use of dimethyl formamide and alkali metal carbonates as solvent resulted in dimer formation, which also contributed to low yield.

SUMMARY OF THE INVENTION

The aim of the present invention is, therefore, to provide an improved process for the preparation of telmisartan. In particular, it is an aim of the present invention to prepare telmisartan in a one step process, thereby increasing the yield, decreasing the cost and avoiding filtration and drying problems.

Surprisingly, it has been found according to the present invention that telmisartan can be synthesised in one step from intermediates [1H-Benzimidazole-2-n-propyl-4-methyl-6-(1'-methyl benzimidazole-2'-yl)] and methyl-4-(bromomethyl)biphenyl-2-carboxylate.

According to the present invention, therefore, there is provided a process for the preparation of telmisartan of formula (I), or a pharmaceutically acceptable salt thereof:

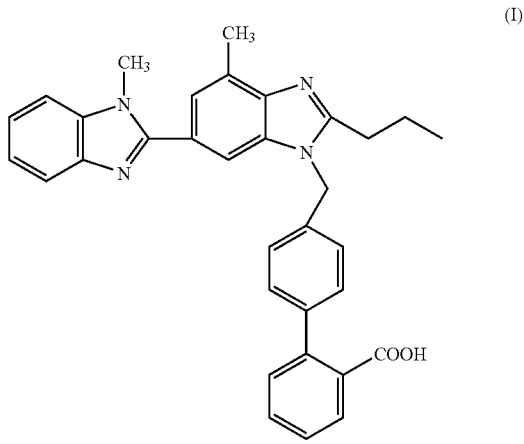 [SMILES: CCCc1nc2c(C)cc(-c3nc4ccccc4n3C)cc2n1Cc1ccc(-c2ccccc2C(=O)O)cc1]

characterised in that 1H-Benzimidazole-2-n-propyl-4-methyl-6-(1'-methyl benzimidazole2'yl) of formula (II), and methyl-4-(bromomethyl)biphenyl-2-carboxylate of formula (III), are subjected to condensation and hydrolysis in a single step (in other words, a "one pot" synthesis):

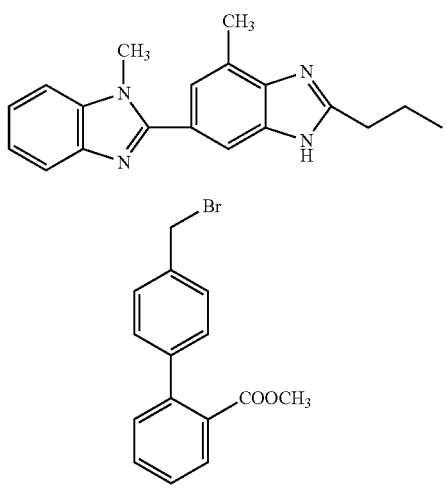

Intermediate compounds of formulae (II) and (III) are preferably reacted according to a process of the present invention in a polar aprotic solvent in the presence of a base. Polar aprotic solvents are well known in the art and can include, for example, dimethyl acetamide, dimethyl formamide, dimethyl sulphoxide, and the like, with the use of dimethyl formamid or dimethyl sulphoxide being preferred, especially dimethyl sulphoxide. Preferred bases for use in a method according to the present invention are alkali metal hydroxides.

DETAILED DESCRIPTION OF THE INVENTION

A process according to the present invention is preferably carried out at a temperature in the range of about 10 to 80° C., with a preferred temperature being in the range of about 25 to 50° C. The reaction time for a process according to the present invention is typically in the range of from about a few minutes to a few hours, depending on the exothermicity of the reaction. Telmisartan is then typically isolated from the reaction mass by adjusting the pH using aqueous acids, suitably for example the pH is adjusted to be in the range of about 3 to 4.5 using acetic acid, optionally followed by extraction in a water-immiscible solvent.

Telmisartan can be isolated directly after pH adjustment by filtration without proceeding to extraction in a water-immiscible solvent. However, the use of the extraction phase is preferred because telmisartan as obtained directly after pH adjustment can be slimy in nature, thereby resulting in slow filtration properties. It is therefore preferable to extract telmisartan into a suitable solvent and isolate it from a non-solvent. A preferred water-immiscible solvent for extraction can be any of dichloromethane, ethyl acetate, chloroform or any other suitable water-immiscible solvent, with the use of dichloromethane being preferred. The organic layer is then suitably concentrated and isolated by addition of a suitable solvent, such as methanol, acetone, diisopropyl ether, acetonitrile or isopropyl acetate, with the use of acetone being preferred.

The present invention further provides telmisartan, or a pharmaceutically acceptable salt thereof, prepared by a process substantially as hereinbefore described. Telmisartan as prepared and isolated (typically employing acetone) by a process according to the present invention advantageously comprises free flowing polymorphic Form A, which can be similarly characterised by the melting point and IR properties as described above for Form A as defined in US 2002/0094997. Telmisartan Form A as provided by the present invention, however, is preferable over telmisartan Form A as prepared by prior art methods, in view of the free flowing properties of telmisartan as provided by the present invention compared to the poor flow characteristics of telmisartan Form A as provided by the prior art, for which the filtration rate can be very slow.

Telmisartan Form A as prepared by a process according to the present invention advantageously has a purity of at least about 97% and is typically obtained in a yield of about 80-88%.

The invention may also comprise further purification of telmisartan so as to achieve a highly pure compound. Preferably, telmisartan is subjected to purification by dissolving it in methanol and a methanolic ammonia mixture and isolating. Preferably, isolation is done by adjusting the pH using acetic acid, suitably to a pH of 3.5-4.0.

According to a preferred embodiment of the present invention, it may be desirable to isolate telmisartan as a pharmaceutically acceptable salt, such as the sodium or potassium salt of telmisartan. Telmisartan in salt form is suitably isolated from the reaction mass prior to pH adjustment.

Telmisartan, or a pharmaceutically acceptable salt thereof, has pharmaceutical utility as an angiotensin II receptor antagonist, and in view of the pharmacological properties thereof, telmisartan, or a pharmaceutically acceptable salt thereof, is suitable for the treatment of hypertension and cardiac insufficiency and also for treating ischaemic peripheral circulatory disorders, myocardial ischaemia (angina), for the prevention of the progression of cardiac insufficiency after myocardial infarction and for treating diabetic nephropathy, glaucoma, gastrointestinal diseases and bladder diseases. In particular, telmisartan, or a pharmaceutically acceptable salt thereof, as provided by the present invention is useful for the treatment of hypertension.

Telmisartan, or a pharmaceutically acceptable salt thereof, as provided by the present invention is also suitable for treating pulmonary diseases, e.g. lung oedema and chronic bronchitis, for preventing arterial restenosis after angioplasty, for preventing thickening of blood vessel walls after vascular operations, and for preventing arteriosclerosis and diabetic angiopathy. In view of the effects of angiotensin on the release of acetyl-choline and dopamine in the brain, telmisartan, or a pharmaceutically acceptable salt thereof, as provided by the present invention is also suitable for alleviating central nervous system disorders, e.g. depression, Alzheimer's disease, Parkinson syndrome, bulimia and disorders of cognitive function.

The present invention further provides, therefore, a pharmaceutically acceptable composition for administering to a patient, suffering from, or susceptible to, a disease state prevented, ameliorated or eliminated by the administration of an angiotensin II receptor antagonist, which composition comprises a therapeutically effective amount of telmisartan, or a pharmaceutically acceptable salt thereof, prepared according to the present invention, together with a pharmaceutically acceptable carrier, diluent or excipient therefor.

As used herein, the term "therapeutically effective amount" means an amount of telmisartan, or a pharmaceutically acceptable salt thereof, which is capable of preventing, ameliorating or eliminating a disease state for which administration of an angiotensin II receptor antagonist is indicated.

By "pharmaceutically acceptable composition" it is meant that the carrier, diluent or excipient is compatible with telmisartan, or a pharmaceutically acceptable salt thereof, and not deleterious to a recipient thereof. For this purpose, telmisartan, or a pharmaceutically acceptable salt thereof, optionally in conjunction with other active substances, such as hypotensives, diuretics and/or calcium antagonists, may be incorporated together with one or more inert conventional carriers and/or diluents, for example with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene-glycol, cetylstearyl alcohol, carboxymethylcellulose or fatty substances such as hard fat or suitable mixtures thereof, in conventional pharmaceutical preparations such as plain or coated tablets, capsules, powders, suspensions or suppositories.

The pharmaceutical compositions of the present invention may be prepared by conventional methods known in the art. For example, tablets may be prepared by mixing telmisartan, or a pharmaceutically acceptable salt thereof, according to the present invention, with known adjuvants and/or diluents and subsequently compressing the mixture in a conventional tabletting machine. The particular dosage form of telmisartan, or a pharmaceutically acceptable salt thereof, required to treat a disease state prevented, ameliorated or eliminated by the administration of an angiotensin II receptor antagonist as described herein in a patient, will depend on the particular disease state or condition, and the symptoms and severity thereof. Dosage, routes of administration, and frequency of dosing are best decided by an attending physician.

The present invention further provides telmisartan, or a pharmaceutically acceptable salt thereof, prepared according to the present invention, for use in the manufacture of a medicament for the treatment of a disease state prevented, ameliorated or eliminated by the administration of an angiotensin II receptor antagonist as described herein.

The present invention also provides a method of treating a disease state prevented, ameliorated or eliminated by the administration of an angiotensin II receptor antagonist in a patient in need of such treatment, which method comprises administering to the patient a therapeutically effective amount of telmisartan, or a pharmaceutically acceptable salt thereof, prepared according to the present invention, substantially as hereinbefore described.

EXAMPLES

The present invention will now be further illustrated by the following Examples, which do not limit the scope of the invention in any way.

Example I

Preparation of [4'-[2-n-propyl-4-methyl-6-(1-methyl benzimidazol-2-yl)benzimidazol-1-yl methyl]biphenyl-2-carboxylic acid]

50 gm of [1H-Benzimidazole-2-n-propyl-4-methyl-6-(1'methyl benzimidazole-2'-yl)] was added to 200 ml dimethyl sulfoxide and 50 gm of potassium hydroxide. To this was added 60 gm of methyl-4-(bromomethyl)biphenyl-2-carboxylate at ambient temperature. The contents were stirred for 2 hours at 25-30° C., then heated to 40-50° C. and maintained for 2 hours. About 500 ml water was added to the reaction mixture at room temperature and acidified to pH 4 with acetic acid. The reaction mixture was filtered and washed with purified water, dried under reduced pressure at 50-60° C. to give 80 gm (88%) of the title product.

Example 2

Preparation of [4'-[2-n-propyl-4-methyl-6-(1-methyl benzimidazol-2-yl)benzimidazol-1-yl methyl]biphenyl-2-carboxylic acid]

50 gm of [1H-Benzimidazole-2-n-propyl-4-methyl-6-(1% methyl benzimidazole-2'-yl)] was added to 200 ml dimethyl sulphoxide and 50 gm of potassium hydroxide. To this was added 60 gm of methyl-4-(bromomethyl)biphenyl-2-carboxylate at ambient temperature. The contents were stirred for 2 hours at 25-30° C. The contents were heated to 40-50° C. and maintained for 2 hours. About 500 ml water was added to the reaction mixture at room temperature and acidified with acetic acid to pH 3.8, extracted twice with 250 ml of dichloromethane and the combined extracts were concentrated and isolated by filtration after addition of 300 ml acetone, dried under reduced pressure at 50-60° C. to give 75 gm (80%) of the title product.

Example 3

Preparation of [4'-[2-n-propyl-4-methyl-6-(1-methyl benzimidazol-2-yl)benzimidazol-1-yl methyl]biphenyl-2-carboxylic acid]

50 gm of [1H-Benzimidazole-2-n-propyl-4-methyl-6-(1'-methyl benzimidazole-2'-yl)] was added to 200 ml dimethyl sulfoxide and 50 gm of sodium hydroxide. To this was added 60 gm of methyl-4-(bromomethyl)biphenyl-2-carboxylate at ambient temperature. The contents were stirred for 2 hours at 25-30° C. and then heated to 40-50 and maintained for 2 hours. About 500 ml water was added to the reaction mixture and acidified with acetic acid to pH 4.2, extract4ed twice with 250 ml of dichloromethane and the combined extracts were concentrated and isolated by filtration after addition of 300 ml acetone, dried under reduced pressure at 50-60° C. to give 75.0 gm (80%) of the title compound.

Example 4

Purification of [4'-[2-n-propyl-4-methyl-6-(1-methyl benzimidazol-2-yl)benzimidazol-1-yl methyl]biphenyl-2-carboxylic acid]

50 gm of [4'-[2-n-propyl-4-methyl-6-(1-methyl benzimidazol-2-yl)benzimidazol-1-yl methyl]biphenyl-2-carboxylic acid] (obtained according to any of Examples 1, 2 or 3) was added to 500 ml of methanol. To this was slowly added 50 ml of methanolic ammonia (10-15%) at 25-30° C. The contents were stirred for 30 minutes at 25-30° C. About 3 gm charcoal was added and stirred at 25-30° C. for 30 minutes. The reaction mixture was filtered over hyflo, bed washed with methanol. The clear filtrate pH was adjusted to 3.5-4.0 using acetic acid. The contents were stirred at 20-30° C. for 1 hour. Pure telmisartan was isolated by filtration, dried under reduced pressure at 50-60° C. to yield 45 gm (90%) of the title product with HPLC purity of about 99.3%.

The invention claimed is:

1. A process for the preparation of telmisartan of formula (I), or a pharmaceutically acceptable salt thereof:

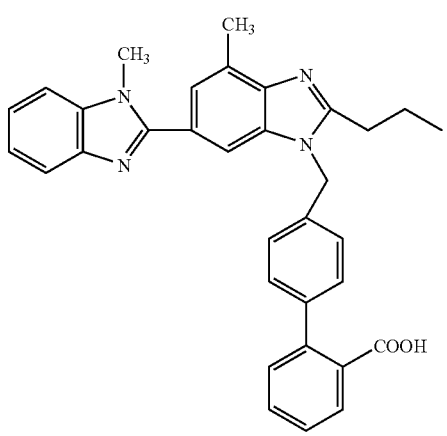

characterised in that 1H-Benzimidazole-2-n-propyl-4-methyl-6-(1'methyl benzimidazole-2'yl) of formula (II) and methyl-4-(bromomethyl)biphenyl-2-carboxylate of formula (III) are subjected to condensation and hydrolysis in a single step:

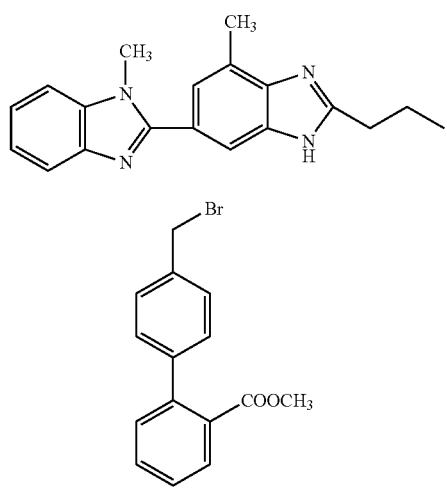

followed by pH adjustment using an aqueous acid,
wherein intermediate compounds of formulae (II) and (III) are reacted in dimethyl sulphoxide in the presence of a base,
wherein further to pH adjustment telmisartan is extracted into dichloromethane and then isolated from acetone, and
which prepares telmisartan Form A.

2. The process according to claim 1, wherein said base is an alkali metal hydroxide.

3. The process according to claim 1, which is carried out at a temperature in the range of about 10 to 80° C.

4. The process according to claim 3, which is carried out at a temperature in the range of about 25 to 50° C.

5. The process according to claim 1, wherein said pH is adjusted to be in the range of about 3 to 4.5.

6. The process according to claim 1, wherein said aqueous acid is acetic acid.

7. The process according to claim 1, wherein telmisartan is isolated as a free acid.

8. The process according to claim 7, wherein telmisartan free acid is optionally converted to a pharmaceutically acceptable salt thereof.

9. The process according to claim 8, wherein telmisartan is the sodium or potassium salt thereof.

10. The process according to claim 1, which prepares telmisartan, or a pharmaceutically acceptable salt thereof, with a purity of at least about 97%.

11. The process according to claim 1, which prepares telmisartan, or a pharmaceutically acceptable salt thereof, in a yield of about 80-88%.

12. The process according to claim 2, which is carried out at a temperature in the range of about 10 to 80° C.

13. The process according to claim 2, wherein said pH is adjusted to be in the range of about 3 to 4.5.

14. The process according to claim 12, wherein said aqueous acid is acetic acid.

15. The process according to claim 13, wherein said aqueous acid is acetic acid.

16. The process according to claim 12, which prepares telmisartan, or a pharmaceutically acceptable salt thereof, with a purity of at least about 97%.

17. The process according to claim 12, which prepares telmisartan, or a pharmaceutically acceptable salt thereof, in a yield of about 80-88%.

18. The process according to claim 13, which prepares telmisartan, or a pharmaceutically acceptable salt thereof, with a purity of at least about 97%.

19. The process according to claim 13, which prepares telmisartan, or a pharmaceutically acceptable salt thereof, in a yield of about 80-88%.

20. The process according to claim 14, which prepares telmisartan, or a pharmaceutically acceptable salt thereof, with a purity of at least about 97%.

21. The process according to claim 14, which prepares telmisartan, or a pharmaceutically acceptable salt thereof, in a yield of about 80-88%.

* * * * *

UNITED STATES PATENT AND TRADEMARK OFFICE
CERTIFICATE OF CORRECTION

PATENT NO. : 8,691,999 B2  Page 1 of 1
APPLICATION NO. : 11/568898
DATED : April 8, 2014
INVENTOR(S) : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1439 days.

Signed and Sealed this

Twenty-ninth Day of September, 2015

Michelle K. Lee
*Director of the United States Patent and Trademark Office*